(12) United States Patent
Plos et al.

(10) Patent No.: US 7,175,671 B2
(45) Date of Patent: Feb. 13, 2007

(54) USE OF NINHYDRIN DERIVATIVES BEARING AN UNSATURATED SYSTEM FOR DYEING KERATIN MATERIAL

(75) Inventors: Grégory Plos, Tokyo (JP); Luc Gourlaouen, Asnieres (FR)

(73) Assignee: L'Oreal S.A., Paris (FR)

( * ) Notice: Subject to any disclaimer, the term of this patent is extended or adjusted under 35 U.S.C. 154(b) by 375 days.

(21) Appl. No.: 10/898,228

(22) Filed: Jul. 26, 2004

(65) Prior Publication Data

US 2005/0060817 A1 Mar. 24, 2005

Related U.S. Application Data

(60) Provisional application No. 60/499,391, filed on Sep. 3, 2003.

(30) Foreign Application Priority Data

Jul. 25, 2003 (FR) .................. 03 09173
Mar. 4, 2004 (FR) .................. 04 02243

(51) Int. Cl.
*A61K 7/13* (2006.01)
(52) U.S. Cl. .................. 8/405; 8/406; 8/407; 8/410; 8/411; 8/421; 8/437; 8/607; 568/327
(58) Field of Classification Search .................. 8/405, 8/406, 407, 410, 411, 421, 437, 607; 568/327
See application file for complete search history.

(56) References Cited

FOREIGN PATENT DOCUMENTS

| DE | 43 17 855 A | 12/1994 |
| DE | 4317855 A1 * | 12/1994 |
| DE | 197 17 222 | 10/1998 |
| DE | 197 45 355 | 4/1999 |
| DE | 198 45 481 | 4/2000 |

OTHER PUBLICATIONS

English Abstract of the Patent No. DE 4317855 A1.*
STIC Search Report (Aug. 4, 2006).*
Hauze, et al. "New Reagents for the Development of Fingerprints"; Jun. 26-30, 1995, Ne'urim, Israel; Hemed Press, 1995, 119-123.
Database WPI, Derwent Publications Ltd., London, GB; AN 1973-22659U, XP002285499.
English language Derwent Abstract of DE 43 17 855 A, Dec. 1, 1994.

* cited by examiner

*Primary Examiner*—Eisa Elhilo
(74) *Attorney, Agent, or Firm*—Finnegan, Henderson, Farabow, Garrett & Dunner, L.L.P.

(57) ABSTRACT

The invention relates to the use for of compositions dyeing keratin materials containing, in a medium that is suitable for dyeing, at least one compound of formula (I)

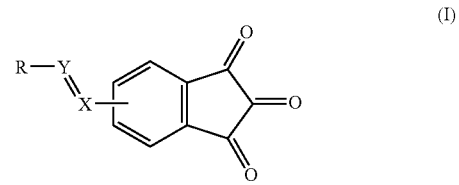

in which X and Y, independently of one another, are chosen from a CH group and a nitrogen atom, R is chosen from aromatic mono- or poly-cyclic groups with fused or non-fused rings, wherein the groups have at least 5 members and optionally comprise at least one hetero atom chosen from nitrogen, oxygen, sulphur and phosphorus. Processes and kits using these compositions are also disclosed.

26 Claims, No Drawings

USE OF NINHYDRIN DERIVATIVES BEARING AN UNSATURATED SYSTEM FOR DYEING KERATIN MATERIAL

This application claims benefit of U.S. Provisional Application No. 60/499,391, filed Sep. 3, 2003.

The present disclosure relates to compositions for dyeing keratin materials, specifically, hair dye compositions containing at least one ninhydrin compound bearing an unsaturated system, optionally combined with a compound containing a primary or secondary amine function or a compound containing an activated methylene function, to a dyeing process using such compositions and to a multi-component coloring agent for performing such a process.

It is common, and has been for many years, for people to wish to modify the color of their skin, their eyelashes or their hair, for example to mask their grey hair. Several techniques have been developed to do this.

It is known practice to dye human keratin fibers, such as the hair, with dye compositions containing oxidation dye precursors, which are generally known as oxidation bases. These oxidation bases are colorless or weakly colored compounds which, when combined with oxidizing products, give rise to colored compounds by a process of oxidative condensation. These dyes are insoluble and are trapped inside the hair fiber.

It is also known that the shades obtained with these oxidation bases can be varied by combining them with couplers or coloration modifiers. The variety of molecules used as oxidation bases and couplers allows a wide range of colors to be obtained.

The colorations obtained may show good shampoo-fastness. However, the oxidation reaction takes place using oxidizing products such as aqueous hydrogen peroxide solution in basic medium. These oxidizing agents may attack the keratin of the hair, the cosmetic and mechanical properties of which may become greatly degraded in the case of repeated colorations.

It is also known practice to dye human keratin fibers by direct dyeing, which comprises applying to the keratin fibers direct dyes, which are colored and coloring molecules that have affinity for the fibers. Examples of direct dyes conventionally used that may be mentioned include nitro dyes, benzene dyes, anthraquinone dyes, nitropyridine dyes, azo dyes, cationic azo dyes, xanthene dyes, acridine dyes, azine dyes, triaryl-methane dyes or natural dyes.

Although the colorations thus obtained are certainly very chromatic and may not cause any chemical degradation of keratin, they have the drawback of being only temporary or semi-permanent, i.e., they may fade out after only 4 to 5 shampoo washes.

There is consequently still a desire for dyeing systems and processes that can give fast results without involving the use of oxidizing agents that may degrade the keratin materials.

The present inventors have found that the use of ninhydrin compounds bearing an unsaturated system and described in greater detail below makes it possible to dye keratin fibers, such as the hair, with fastness equivalent to or greater than that obtained by oxidation dyeing, and in the absence of strong oxidizing agents, thus making it possible to keep the keratin materials from degrading.

The ninhydrin compounds bearing an unsaturated system and mentioned above may, in some embodiments, be used in combination with compounds containing labile hydrogen, such as primary or secondary amines or compounds containing an activated methylene function.

The colorations thus obtained may show good chromaticities and may be distinguished by excellent wash-fastness (several tens of shampoo washes).

One aspect of the present disclosure is thus a process for dyeing keratin materials comprising applying to the keratin materials a composition comprising, in a medium that is suitable for dyeing, at least one compound of formula (I) or the tautomer thereof:

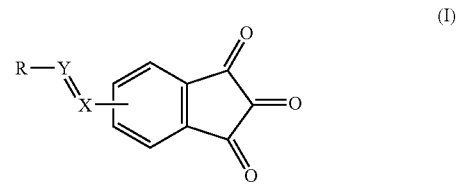

wherein

X and Y, independently of one another, are chosen from a CH group and a nitrogen atom, R is chosen from aromatic monocyclic and polycyclic groups with fused or non-fused rings, said groups having at least 5 members and optionally comprising at least one hetero atom chosen from nitrogen, oxygen, sulphur and phosphorus.

In one embodiment, R is chosen from pyrrolyl, thiophenyl, furanyl, pyrazolyl, imidazolyl, phenyl, pyranyl, pyridyl, pyrimidinyl, indolyl, quinolyl, carbazolyl, chromenyl, biphenyl, and naphtalenyl groups. For example, R may be chosen from phenyl groups and naphthalenyl groups.

The group R may be substituted with at least one group chosen from halo groups, such as chloro, iodo, bromo and/or fluoro, $C_1$–$C_6$ alkyl groups, hydroxyl groups, $C_1$–$C_6$ alkoxy groups, amino groups, mono- or di($C_1$–$C_6$ alkyl)amino groups, mono- or dihydroxy($C_1$–$C_6$ alkyl)amino groups, tri($C_1$–$C_6$ alkyl)ammonio groups, imidazolyl groups, pyridyl groups thio groups, ($C_1$–$C_6$ alkyl)thio groups, thio ($C_1$–$C_6$ alkyl)groups, ($C_1$–$C_6$ alkyl)carbonyl groups, hydrogenocarbonyl groups, hydroxycarbonyl groups, ($C_1$–$C_6$ alkoxy)carbonyl groups, nitro groups and sulphonato groups, and the corresponding protonated groups such as ammonio, imidazolio and/or pyridinio.

Such compositions are useful, for example, for dyeing keratin fibers, such as the hair.

The ninhydrin compounds of formula (I) above are used as disclosed herein in a cosmetically acceptable medium comprising a large fraction of water. When they are dissolved in such an aqueous medium, the ninhydrin compounds of formula (I) are in hydration equilibrium with the gem-diol (or carbonyl hydrate) form corresponding to formula (Ia) below:

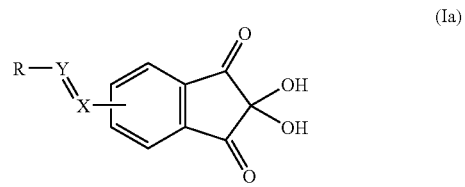

When reference is made, in the present disclosure, to ninhydrin compounds of formula (I), such references always include not only the compounds of formula (I) but also the corresponding hydrated forms of formula (I)a.

Examples of ninhydrin compounds that may be used in accordance with the present disclosure for dyeing keratin fibers include, but are not limited to, the following:

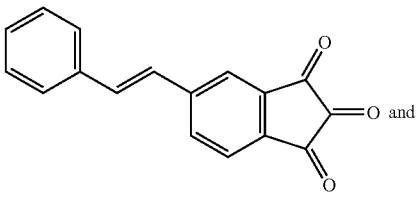

(a) 5-cinnamylninhydrin

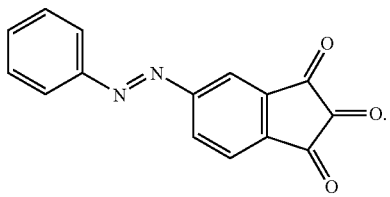

(b) 5-phenylazoninhydrin

The ninhydrin compounds used herein are known. The synthesis of the above ninhydrin compounds (a) and (b) is described in the following publications: (a) Hauze D. B., Petrovskaia O., Joulliée M. M., Hark R. R., New reagents for the development of fingerprints in Almog J., Springer E., ed. Proceedings of the International Symposium on Fingerprint Detection and Identification, Ne'urim, Israel: Hemed Press, 1995, 119–123; and (b) Taylor B. M., Ph. D. Dissertation Thesis, Flinders University 1997.

In accordance with the present disclosure, the ninhydrin compounds of formula (I) described above may be used alone for dyeing keratin materials. The reason for this is that these compounds are capable of generating colored molecules with the amine functions of keratin (colored reaction).

Compounds of formula (I) may also be used in combination with at least one activator, which makes it possible to modify the reaction kinetics of the ninhydrin compound with the keratin material. Such an activator may be chosen from, for example, oxidizing agents, reducing agents, Brönstedt acids, metal catalysts such as catalysts based on a transition metal such as iron, platinum or palladium, proteins, such as enzymes, compounds that modify the ionic strength of the medium, such as NaCl salts, compounds containing labile hydrogen chosen from those comprising a primary or secondary amine function and those comprising an activated methylene function. Needless to say, a mixture of such compounds may also be used.

The compounds containing a primary amine or secondary amine function may be, for example, aromatic amines.

Examples of such aromatic amines that may be mentioned include N,N-dimethyl-p-phenylenediamine, N,N-diethyl-p-phenylenediamine, N-(2-hydroxyethyl)-N-ethyl-p-phenylenediamine, N,N,-bis(2-hydroxyethyl)-p-phenylenediamine, N-(2-methoxyethyl)-p-phenylenediamine, 2,3-, 2,4- or 2,5-dichloro-p-phenylenediamine, 2-chloro-p-phenylenediamine, 2,5-dihydroxy-4-morpholinoaniline dihydrobromide, 2-, 3- or 4-aminophenol, 2-aminomethyl-4-aminophenol, 2-hydroxymethyl-4-aminophenol, ortho-phenylenediamine, p-phenylenediamine, ortho-toluenediamine, 2,5-diaminotoluene, 2,5-diaminophenol, 2,5-diaminophenethol, 4-amino-3-methylphenol, 2-(2,5-diaminophenyl)ethanol, 2,4-d iaminophenoxyethanol, 2-(2, 5-d iaminophenoxy)ethanol, 4-methylaminoaniline, 3-amino-4-(2'-hydroxyethyloxy)aniline, 3,4-methylenediaminoaniline, 3,4-methylenedioxyaniline, 3-amino-2,4-dichlorophenol, 4-methylaminophenol, 2-methyl-5-aminophenol, 3-methyl-4-aminophenol, 2-methyl-5-(2-hydroxyethylamino)phenol, 6-methyl-3-amino-2-chlorophenol, 2-methyl-5-amino-4-chlorophenol, 3,4-methylene-dioxyphenol, 5-(2-hydroxyethylamino)-4-methoxy-2-methylphenol, 4-amino-2-hydroxymethylphenol, 1,3-diamino-2,4-dimethoxybenzene, 2-, 3- or 4-aminobenzoic acid, 2-amino-, 3-amino- or 4-aminophenylacetic acid, 2,3-, 2,4-, 2,5-, 3,4- or 3,5-diaminobenzoic acid, 4-amino- or 5-aminosalicylic acid, 3-amino-4-hydroxybenzoic acid, 4-amino-3-hydroxybenzoic acid, 2-amino, 3-amino- or 4-aminobenzenesulphonic acid, 3-amino-4-hydroxybenzenesulphonic acid, 4-amino-3-hydroxynaphthalene-1-sulphonic acid, 6-amino-7-hydroxynaphthalene-2-sulphonic acid, 7-amino-4-hydroxynaphthalene-2-sulphonic acid, 4-amino-5-hydroxynaphthalene-2, 7-disulphonic acid, 3-amino-2-naphthoic acid, 3-aminophthalic acid, 5-aminoisophthalic acid, 1,3,5-triaminobenzene, 1,2,4-triaminobenzene, 1,2,4,5-tetraaminobenzene, 2,4,5-triaminophenol, pentaaminobenzene, hexaaminobenzene, 2,4,6-triaminoresorcinol, 4,5-diaminopyrocatechol, 4,6-diaminopyrogallol, 3,5-diamino-4-hydroxypyrocatechol, and aromatic anilines and aromatic phenols comprising another aromatic residue, corresponding to formula (II)

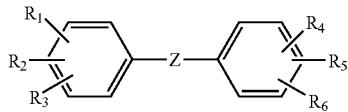

II wherein $R^1$ is chosen from a hydroxyl group and an amino group optionally substituted with a group chosen from $C_{1-4}$ alkyl, $C_{1-4}$ hydroxyalkyl and $(C_{1-4}$ alkoxy)$(C_{1-4}$ alkyl) groups, $R^2$, $R^3$, $R^4$, $R^5$ and $R^6$ are each independently chosen from a hydrogen atom; a hydroxyl group and an amino group, optionally substituted with a group chosen from $C_{1-4}$ alkyl, $C_{1-4}$ hydroxyalkyl, and $(C_{1-4}$ alkoxy)$(C_{1-4}$ alkyl) groups; and carboxylic and sulphonic acid groups;

Z is chosen from a direct bond, a saturated or unsaturated, optionally hydroxylated $C_{1-4}$ hydrocarbon-based chain, a group chosen from carbonyl, sulphonyl and imino groups, an atom chosen from oxygen and sulphur atoms, and groups of formula Q—(CH$_2$—P—CH$_2$—Q')$_o$ in which P is chosen from a direct bond, or a —CH$_2$— group, and a —CHOH— group, Q and Q' are chosen, independently of each other, from oxygen atoms, groups NR$^7$ in which R$^7$ is chosen from a hydrogen atom, a $C_{1-4}$ alkyl group, and a $C_{1-4}$ hydroxyalkyl group, and a group O—(CH$_2$)$_p$NH or NH—(CH$_2$)$_p$'—O in which p and p' are equal to 2 or 3 and 0 is a number from 1 to 4.

The non-aromatic primary or secondary amines are, for example, chosen from 2-aminoethanol, 2-methoxyethylamine, 2-ethoxyethylamine, 2-(2-aminoethoxy)ethanol, 2- or 3-aminopropanol, 2,3-dihydroxypropylamine, 4-hydroxypropyl-amine, 2-aminopropane-1,3-diol, 2-amino-2-methylpropanol, 2-amino-2-methylpropane-1,3-diol, 2-amino-2-hydroxymethylpropane-1,3-diol, tetrahydropentylamine, pentahydroxyhexylamines such as glucamine, D-glucosamine, D-galactosamine, 1,2-diaminoethane, 1,2- or 1,3- diaminopropane, 1,3-diamino-2-propanol, 2-(2-aminoethylamino)ethylamine, 2-(2-aminoethylamino)ethanol, 3-(2-aminoethylamino)propylamine, and 3-(2-aminoethylamino) propanol.

The compounds comprising an activated methylene function are chosen, for example, from the following: 1,2,3,3-tetramethyl-3H-indolium iodide, 1,2,3,3-tetramethyl-3H-indolium p-toluenesulphonate, 1,2,3,3-tetramethyl-3H-indolium methanesulphonate, 1,3,3-trimethyl-2-methyleneindoline, 2,3-dimethylbenzothiazoliu m iodide, 2,3-dimethylbenzothiazolium p-toluenesulphonate, rhodanine, rhodanine-3-acetic acid, 1-ethyl-2-quinaldinium iodide, 1-methyl-2-quinaldinium iodide, barbituric acid, thiobarbituric acid, 1,3-dimethylthiobarbituric acid, diethylthiobarbituric acid, oxindole, 3-indoxyl acetate, coumarone and 1-methyl-3-phenyl-2-pyrazolinone.

These primary and secondary amines and these compounds containing activated methylene functions, and also other compounds containing labile hydrogen, are described also in patent applications DE 43 17 855, DE 197 17 222, DE 198 45 481 and DE 197 45 355, in which they are used for dyeing keratin fibers in combination with compounds other than the ninhydrin compounds of formula (I).

When the ninhydrin compounds of formula (I) are used in combination with a primary or secondary amine or with a compound containing an activated methylene function, these various reagents should be stored separately in order to avoid a premature colored reaction. The reagents are thus placed in contact only immediately before application to the hair, by extemporaneous mixing of two compositions containing, respectively, the ninhydrin compound(s) and the compound(s) containing labile hydrogen. The reagents may also be placed in contact directly on the hair by successive application of the various reagents.

A subject of the present disclosure is consequently also a multi-component coloring agent comprising
- as first component, a composition (a) comprising at least one ninhydrin compound of formula (I), and
- as second component, a composition (b) comprising at least one compound chosen from compounds comprising a primary or secondary amine function and compounds comprising an activated methylene function, as described above.

Also disclosed herein is a multi-compartment kit, with at least one first compartment containing the first component (composition (a)) and at least one second compartment containing the second component (composition (b)).

Yet another subject of the present disclosure is a cosmetic dye composition comprising at least one ninhydrin compound of formula (I) and at least one cosmetic active principle.

The cosmetic active principles present in the cosmetic compositions disclosed herein may be chosen, for example, from vitamins, saccharides, oligosaccharides, hydrolysed or non-hydrolysed, modified or unmodified polysaccharides, amino acids, oligopeptides, peptides, hydrolyzed or non-hydrolyzed, modified or unmodified proteins, polyamino acids, enzymes, branched or unbranched fatty acids and fatty alcohols, animal, plant or mineral waxes, ceramides and pseudoceramides, hydroxylated organic acids, UV-screening agents, antioxidants, free-radical scavengers, chelating agents, antidandruff agents, seborrhoea regulators, calmatives, cationic, anionic, nonionic or amphoteric surfactants, cationic, anionic, neutral or amphoteric polymers, organomodified or non-organomodified silicones, mineral, plant or animal oils, polyisobutenes, and poly(α-olefins), fatty esters, anionic polymers in dissolved or dispersed form, nonionic polymers in dissolved or dispersed form, reducing agents, solvents, hair dyes such as direct dyes or oxidation dye precursors (bases and/or couplers) other than the claimed compounds containing a primary or secondary amine function, oxidizing agents such as hydrogen peroxide optionally combined with persalts, and pigments, and mixtures thereof.

The cosmetic active principle is present in the composition in an amount ranging from 0.001% to 50% by weight, for example, from 0.01% to 20% by weight, such as from 0.1% to 10% by weight relative to the total weight of the cosmetic composition.

In one embodiment, the cosmetic active principle is a surfactant and/or a polymer, these agents possibly being of nonionic, cationic, anionic or amphoteric nature.

The dye compositions disclosed above are generally stable on storage when they contain, as sole reagents, ninhydrin compounds of formula (I). However, when they contain both ninhydrin compounds of formula (I) and compounds containing labile hydrogen such as primary or secondary amines or compounds containing an activated methylene function, these compositions should be used immediately after mixing the at least one ninhydrin compound of formula (I) with the compound(s) containing labile hydrogen.

These ready-to-use dye compositions, whether they are stable on storage or prepared immediately before use, may have a pH ranging from 2 to 12, such as from 3 to 11.

Their amount of the at least one ninhydrin compound of formula (I) in the composition ranges from 0.0001% to 30% by weight relative to the total weight of the composition.

The compounds containing labile hydrogen used in combination with the at least one ninhydrin compound of formula (I) are present in an amount ranging from 0.0001% to 30% by weight relative to the total weight of the composition.

Also disclosed herein is a cosmetic composition containing at least one ninhydrin compound of formula (I) and at least one compound chosen from surface-active agents and/or the polymeric agents, these agents being non-ionic, cationic, anionic or amphoteric.

A subject of the present disclosure is also a hair dyeing process comprising the application to the hair of a ready-to-use hair dye composition as described above. This composition is left in contact with the hair fibers for a time that is sufficient to obtain the desired coloration. This leave-in time is generally from 5 minutes to 1 hour, for example, from 15 to 30 minutes. The color reaction between the at least one ninhydrin compound and the amine functions of the keratin or the compounds containing labile hydrogen that are optionally present may be accelerated by heating the hair impregnated with the dye composition. The heating temperature may go up to 80° C., for example, be less than or equal to 60° C.

After obtaining the desired coloration, the hair is rinsed and washed.

When compounds containing labile hydrogen such as primary or secondary amines or compounds containing an activated methylene function are used, the application of the reagents participating in the color reaction may also take place in two stages, in other words two different compositions containing, respectively, at least one ninhydrin compound of formula (I) and at least one compound comprising a primary or secondary amine function or an activated methylene function may be applied successively.

Also disclosed is a two-stage dyeing process comprising the application to the hair one after the other, in any order, of a composition (a) and a composition (b) as defined above for the multi-component coloring agent.

This separate application of two reactive compositions avoids the handling of colored compositions and thus reduces the risks of soiling materials such as clothing.

An intermediate rinsing step may also be inserted between the application of the first composition and the application of the second composition.

Analogously with that described above, the hair impregnated with composition (a) and/or (b) may be heated, for example, up to a temperature of 80° C., such as a temperature not exceeding 60° C., such heating making it possible to accelerate the color reaction and to shorten the leave-in time.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

What is claimed is:

1. A process for dyeing keratin material comprising:
    applying to the keratin material a composition comprising, in a medium that is suitable for dyeing, at least one ninhydrin compound of formula (I):

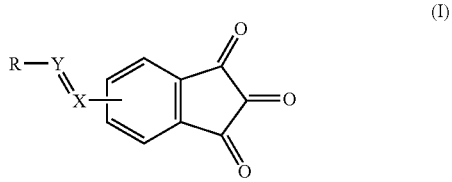

wherein
    X and Y, independently of one another, are chosen from a CH group and a nitrogen atom,
    R is chosen from aromatic mono-cyclic and poly-cyclic groups with fused or non-fused rings, wherein the groups have at least 5-members and optionally comprise at least one hetero atom chosen from nitrogen, oxygen, sulphur and phosphorus atoms.

2. The process according to claim 1, wherein R is chosen from pyrrolyl, thiophenyl, furanyl, pyrazolyl, imidazolyl, phenyl, pyranyl, pyridyl, pyrimidinyl, indolyl, quinolyl, carbazolyl, chromenyl, biphenyl, and naphthalenyl groups.

3. The process according to claim 2, wherein R is chosen from phenyl and naphthalenyl groups.

4. The process according to claim 1, wherein R is substituted with at least one group chosen from halo groups, $C_1$–$C_6$ alkyl groups, hydroxyl groups, $C_1$–$C_6$ alkoxy groups, amino groups, imidazolyl groups, pyridyl groups, mono ($C_1$–$C_6$ alkyl)amino groups, di($C_1$–$C_6$ alkyl)amino groups, monohydroxy($C_1$–$C_6$ alkyl)amino groups, dihydroxy($C_1$–$C_6$ alkyl)amino groups, tri($C_1$–$C_6$ alkyl)ammonio groups, thio groups, ($C_1$–$C_6$ alkyl)thio groups, thio($C_1$–$C_6$ alkyl)groups, ($C_1$–$C_6$ alkyl)carbonyl groups, hydrogenocarbonyl groups, hydroxycarbonyl groups, ($C_1$–$C_6$ alkoxy)carbonyl groups, nitro groups and sulphonato groups, and the corresponding protonated groups thereof.

5. The process according to claim 4, wherein said protonated groups are chosen from ammonio, imidazolio and pyridinio groups.

6. The process according to claim 1, wherein said composition further comprises at least one activator which makes it possible to modify the reaction kinetics of the at least one ninhydrin compound of formula (I) with the keratin material.

7. The process according to claim 6, wherein the at least one activator is chosen from oxidizing agents, reducing agents, Brönsted acids, metal catalysts, proteins, compounds that modify the ionic strength of the medium, and compounds comprising labile hydrogen chosen from those comprising a primary or secondary amine function and those comprising an activated methylene function.

8. The process according to claim 7, wherein the at least one activator is chosen from compounds comprising a primary or secondary amine function and compounds comprising an activated methylene function.

9. The process according to claim 8, wherein the compound comprising a primary or secondary amine function is chosen from
    aromatic amines chosen from N,N-dimethyl-p-phenylenediamine, N,N-diethyl-p-phenylenediamine, N-(2-hydroxyethyl)-N-ethyl-p-phenylenediamine, N,N,-bis(2-hydroxyethyl)-p-phenylenediamine, N-(2-methoxyethyl)-p-phenylenediamine, 2,3-, 2,4- or 2,5-dichloro-p-phenylenediamine, 2-chloro-p-phenylenediamine, 2,5-dihydroxy-4-morpholinoaniline dihydrobromide, 2-, 3- or 4-aminophenol, 2-aminomethyl-4-aminophenol, 2-hydroxymethyl-4-aminophenol, ortho-phenylenediamine, p-phenylenediamine, ortho-toluenediamine, 2,5-diaminotoluene, 2,5-diaminophenol, 2,5-diaminophenethol, 4-amino-3-methylphenol, 2-(2,5-diaminophenyl)ethanol, 2,4-d iaminophenoxyethanol, 2-(2,5-di-aminophenoxy)ethanol, 4-methylaminoaniline, 3-amino-4-(2'-hydroxyethyloxy)aniline, 3,4-methylenediaminoaniline, 3,4-methylenedioxyaniline, 3-amino-2,4-dichlorophenol, 4-methylaminophenol, 2-methyl-5-aminophenol, 3-methyl-4-aminophenol, 2-methyl-5-(2-hydroxyethylamino) phenol, 6-methyl-3-amino-2-chlorophenol, 2-methyl-5-amino-4-chlorophenol, 3,4-methylenedioxyphenol, 5-(2-hydroxyethylamino)-4-methoxy-2-methyl-phenol, 4-amino-2-hydroxymethylphenol, 1,3-diamino-2, 4-dimethoxybenzene, 2-, 3- or 4-aminobenzoic acid, 2-amino-, 3-amino- or 4-aminophenylacetic acid, 2,3-, 2,4-, 2,5-, 3,4- or 3,5-diaminobenzoic acid, 4-amino- or 5-aminosalicylic acid, 3-amino-4-hydroxybenzoic acid, 4-amino-3-hydroxybenzoic acid, 2-amino, 3-amino- or 4-aminobenzenesulphonic acid, 3-amino-4-hydroxybenzenesulphonic acid, 4-amino-3-hydroxynaphthalene-1-sulphonic acid, 6-amino-7-hydroxynaphthalene-2-sulphonic acid, 7-amino-4-hydroxynaphthalene-2-sulphonic acid, 4-amino-5-hydroxynaphthalene-2,7-disulphonic acid, 3-amino-2-naphthoic acid, 3-aminophthalic acid, 5-aminoisophthalic acid, 1,3,5-triaminobenzene, 1,2,4-triaminobenzene, 1,2,4,5-tetraaminobenzene, 2,4,5-triaminophenol, pentaaminobenzene, hexaaminobenzene, 2,4,6-triaminoresorcinol, 4,5-d iaminopyrocatechol, 4,6-diaminopyrogallol, 3,5-diamino-4-hydroxypyrocatechol, and aromatic anilines and aromatic phenols comprising another aromatic residue, corresponding to formula (II) below

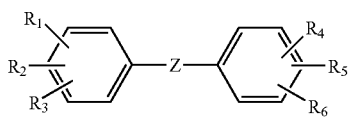

wherein
- $R^1$ is chosen from a hydroxyl group and amino groups optionally substituted with a group chosen from $C_{1-4}$ alkyl, $C_{1-4}$ hydroxyalkyl and $(C_{1-4}$ alkoxy$)(C_{1-4}$ alkyl) groups,
- $R^2, R^3, R^4, R^5$ and $R^6$ each independently are chosen from a hydrogen atom, a hydroxyl group and amino groups, optionally substituted with a group chosen from $C_{1-4}$ alkyl, $C_{1-4}$ hydroxyalkyl and $(C_{1-4}$ alkoxy$)(C_{1-4}$ alkyl) groups and from carboxylic and sulphonic acid groups,
- Z is chosen from a direct bond, a saturated or unsaturated, optionally hydroxylated $C_{1-4}$ hydrocarbon-based chain, a carbonyl group, a sulphonyl group, an imino group, an oxygen atom, a sulphur atom, and a group of formula Q—(CH$_2$—P—CH$_2$—Q')$_o$ in which P is chosen from a direct bond, a —CH$_2$— group, and a —CHOH— group, Q and Q' are chosen from, independently of each other, an oxygen atom, a group NR$^7$ in which R$^7$ is chosen from a hydrogen atom, a $C_{1-4}$ alkyl group, a $C_{1-4}$ hydroxyalkyl group, and a group O—(CH$_2$)$_p$NH or NH—(CH$_2$)$_p$'—O in which p and p' are equal to 2 or 3 and o is a number from 1 to 4, and aliphatic amines chosen from 2-aminoethanol, 2-methoxyethylamine, 2-ethoxy-ethylamine, 2-(2-aminoethoxy)ethanol, 2-amino-propanol, 3-aminopropanol, 2,3-dihydroxypropylamine, 4-hydroxypropylamine, 2-aminopropane-1,3-diol, 2-amino-2-methyl-propanol, 2-amino-2-methylpropane-1,3-diol, 2-amino-2-hydroxymethylpropane-1,3-diol, tetrahydropentylamine, pentahydroxyhexylamines, glucamine, D-glucosamine, D-galactosamine, 1,2-diaminoethane, 1,2- or 1,3-diaminopropane, 1,3-diamino-2-propanol, 2-(2-aminoethylamino)ethylamine, 2-(2-aminoethylamino)ethanol, 3-(2-aminoethylamino)propylamine, and 3-(2-aminoethylamino)propanol.

10. The process according to claim 9, wherein the compound comprising a primary or secondary amine function is chosen from aromatic amines.

11. The process according to claim 8, wherein the activated methylene function is chosen from 1,2,3,3-tetramethyl-3H-indolium iodide, 1,2,3,3-tetramethyl-3H-indolium p-toluenesulphonate, 1,2,3,3-tetramethyl-3H-indolium methanesulphonate, 1,3,3-trimethyl-2-methyleneindoline, 2,3-dimethylbenzothiazolium iodide, 2,3-dimethylbenzothiazolium p-toluenesulphonate, rhodanine, rhodanine-3-acetic acid, 1-ethyl-2-quinaldinium iodide, 1-methyl-2-quinaldinium iodide, barbituric acid, thiobarbituric acid, 1,3-dimethylthiobarbituric acid, diethylthiobarbituric acid, oxindole, 3-indoxyl acetate, coumarone and 1-methyl-3-phenyl-2-pyrazolinone.

12. The process according to claim 1, wherein the composition has a pH ranging from 2 to 12.

13. The process according to claim 12, wherein the pH ranges from 3 to 11.

14. The process according to claim 1, wherein the at least one ninhydrin compound of formula (I) is present in the composition in an amount ranging from 0.0001% to 30% by weight relative to the total weight of the composition.

15. The process according to claim 8, wherein the at least one compound chosen from compounds containing an activated methylene function and compounds containing a primary or secondary amine function is present in the composition in an amount ranging from 0.0001% to 30% by weight relative to the total weight of the composition.

16. A cosmetic dyeing composition comprising, in a medium that is suitable for dyeing keratin fibers,
at least one ninhydrin compound of formula (I):

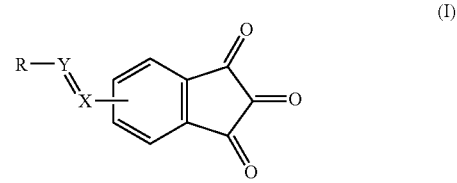

wherein
- X and Y, independently of one another, are chosen from a CH group and a nitrogen atom,
- R is chosen from aromatic mono-cyclic and poly-cyclic groups with fused or non-fused rings, wherein the groups have at least 5-members and optionally comprise at least one hetero atom chosen from nitrogen, oxygen, sulphur and phosphorus atoms and
- at least one agent chosen from nonionic, cationic, anionic and amphoteric surfactants and from nonionic, cationic, anionic or amphoteric polymers.

17. A ready-to-use cosmetic composition comprising:
at least one ninhydrin compound of formula (I):

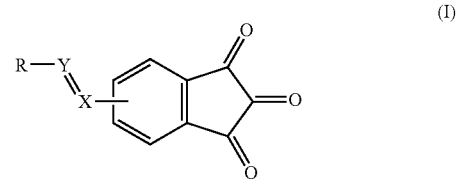

wherein
- X and Y, independently of one another, are chosen from a CH group and a nitrogen atom,
- R is chosen from aromatic mono-cyclic and poly-cyclic groups with fused or non-fused rings, wherein the groups have at least 5-members and optionally comprise at least one hetero atom chosen from nitrogen, oxygen, sulphur and phosphorus atoms, and
- at least one compound chosen from compounds comprising a primary or secondary amine function and compounds comprising an activated methylene function,
wherein the ready-to-use composition is prepared at the time of use.

18. A multi-component coloring agent for keratin material comprising a first component comprising at least one ninhydrin compound of formula (I):

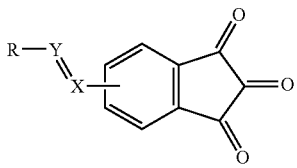

wherein
- X and Y, independently of one another, are chosen from a CH group and a nitrogen atom,
- R is chosen from aromatic mono-cyclic and poly-cyclic groups with fused or non-fused rings, wherein the groups have at least 5-members and optionally comprise at least one hetero atom chosen from nitrogen, oxygen, sulphur and phosphorus atoms, and
- a second component comprising at least one activator which makes it possible to modify the reaction kinetics of the at least one ninhydrin compound of formula (I) with the keratin material.

19. A multi-compartment kit for coloring keratin material comprising:
at least one first compartment comprising at least one ninhydrin compound of formula (I):

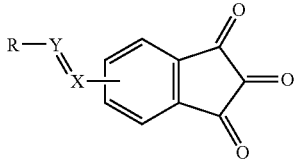

wherein
- X and Y, independently of one another, are chosen from a CH group and a nitrogen atom,
- R is chosen from aromatic mono-cyclic and poly-cyclic groups with fused or non-fused rings, wherein the groups have at least 5-members and optionally comprise at least one hetero atom chosen from nitrogen, oxygen, sulphur and phosphorus atoms, and
- at least one second compartment comprising at least one activator which makes it possible to modify the reaction kinetics of the at least one ninhydrin compound of formula (I) with the keratin material.

20. A process for dyeing hair comprising:
applying to the hair a composition comprising, in a medium that is suitable for dyeing, at least one ninhydrin compound of formula (I):

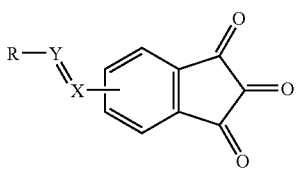

wherein
- X and Y, independently of one another, are chosen from a CH group and a nitrogen atom,
- R is chosen from aromatic mono-cyclic and poly-cyclic groups with fused or non-fused rings, wherein the groups have at least 5-members and optionally comprise at least one hetero atom chosen from nitrogen, oxygen, sulphur and phosphorus atoms, leaving the composition on the hair for a time sufficient to obtain a desired coloration, and
rinsing and washing the hair.

21. The process according to claim 20, further comprising heating the hair impregnated with hair dye composition up to a temperature of 80° C.

22. The process according to claim 21, wherein the hair is heated to a temperature of 60° C.

23. A process for dyeing hair comprising:
applying to the hair
a first composition comprising at least one ninhydrin compound of formula (I):

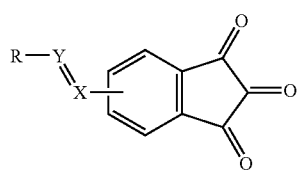

wherein
- X and Y, independently of one another, are chosen from a CH group and a nitrogen atom,
- R is chosen from aromatic mono-cyclic and poly-cyclic groups with fused or non-fused rings, wherein the groups have at least 5-members and optionally comprise at least one hetero atom chosen from nitrogen, oxygen, sulphur and phosphorus atoms, and
- a second composition comprising at least one activator which makes it possible to modify the reaction kinetics of the at least one ninhydrin compound of formula (I) with the hair,
wherein the first and second compositions are applied in any order.

24. A process according to claim 23, wherein an intermediate rinsing step is inserted between the application of the first composition and the application of the second composition.

25. A process according to claim 23, further comprising heating the hair impregnated with the first composition and/or with the second composition up to a temperature of 80° C.

26. The process according to claim 25, wherein the hair is heated to a temperature of 60° C.

* * * * *

UNITED STATES PATENT AND TRADEMARK OFFICE
CERTIFICATE OF CORRECTION

| | |
|---|---|
| PATENT NO. | : 7,175,671 B2 |
| APPLICATION NO. | : 10/898228 |
| DATED | : February 13, 2007 |
| INVENTOR(S) | : Grégory Plos et al. |

It is certified that error appears in the above-identified patent and that said Letters Patent is hereby corrected as shown below:

On the Title Page, Item (57), in the Abstract, line 1,
"use for of compositions dyeing" should read
--use of compositions for dyeing--.

In claim 1, column 7, line 57, "5-members" should read --5 members--.

In claim 9, column 8, lines 45-46, "2,4-d iaminophenoxyethanol,"
should read --2,4-diaminophenoxyethanol,--.

In claim 9, column 9, line 4, "4,5-d iaminopyrocatechol,"
should read --4,5-diaminopyrocatechol,--.

In claim 16, column 10, line 34, "5-members" should read --5 members--.

In claim 17, column 10, line 58, "5-members" should read --5 members--.

In claim 18, column 11, line 18, "5-members" should read --5 members--.

In claim 19, column 11, line 45, "5-members" should read --5 members--.

In claim 20, column 12, line 7, "5-members" should read --5 members--.

In claim 23, column 12, line 44, "5-members" should read --5 members--.

Signed and Sealed this

Tenth Day of April, 2007

JON W. DUDAS
*Director of the United States Patent and Trademark Office*